US008911444B2

(12) United States Patent
Bailey

(10) Patent No.: US 8,911,444 B2
(45) Date of Patent: Dec. 16, 2014

(54) COMPOSITE SURGICAL INSTRUMENT

(75) Inventor: Aaron M. Bailey, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 978 days.

(21) Appl. No.: 12/938,019

(22) Filed: Nov. 2, 2010

(65) Prior Publication Data

US 2012/0109135 A1 May 3, 2012

(51) Int. Cl.
*A61F 5/00* (2006.01)
*A61B 17/15* (2006.01)
*A61B 17/17* (2006.01)

(52) U.S. Cl.
CPC .............. *A61B 17/15* (2013.01); *A61B 17/17* (2013.01); *A61B 17/157* (2013.01); *A61B 17/1764* (2013.01)
USPC .......................................... 606/87

(58) Field of Classification Search
CPC ...... A61B 17/15; A61B 17/17; A61B 17/151; A61B 17/154; A61B 17/155; A61B 17/157; A61B 17/1764
USPC .............................. 606/87, 88, 89, 96, 97, 98
See application file for complete search history.

(56) References Cited

U.S. PATENT DOCUMENTS

| 4,196,237 | A | * | 4/1980 | Patel et al. ........... 427/456 |
| 5,490,854 | A | * | 2/1996 | Fisher et al. ........... 606/88 |
| 5,817,097 | A | | 10/1998 | Howard et al. |
| 7,534,263 | B2 | | 5/2009 | Burdulis, Jr. et al. |
| 2006/0111725 | A1 | | 5/2006 | Biegun |
| 2007/0198022 | A1 | | 8/2007 | Lang et al. |
| 2008/0243127 | A1 | | 10/2008 | Lang et al. |
| 2008/0275452 | A1 | | 11/2008 | Lang et al. |

FOREIGN PATENT DOCUMENTS

WO WO94/14366 A2 7/1994

OTHER PUBLICATIONS

Website: http://www.conformis.com/physicians/image-to-implant-technology/ijig-instrumentation, accessed Sep. 2, 2010.
Website: http://www.conformis.com/physicians/image-to-implant-technology/ifit-technology, accessed Sep. 2, 2010.
Website: http://www.materialise.com/materialise/view/en/2970659-Product+overview.html, accessed Sep. 13, 2010.
Article—Simplified Guide for Precise Implant Placement: A Technical Note, Kennedy et al., The International Journal of Oral Maxillofacial Implants, vol. 13, No. 5, 1998, pp. 684-688.
Article—Three-Dimensional Guidance System for Implant Insertion: Part I, Weinberg et al., Implant Dentistry, vol. 7, No. 2, 1998, pp. 81-91.
"Standard Hardness Conversion Tables for Metals Relationship Among Brinell Hardness, Vickers Hardness, Rockwell Hardness, Superficial Hardness, Knoop Hardness, and Scleroscope Hardness", ASTM International, Designation: E140-07, (Aug. 18, 2010), 21 pgs.

\* cited by examiner

*Primary Examiner* — Anu Ramana
(74) *Attorney, Agent, or Firm* — Schwegman Lundberg & Woessner, P.A.

(57) ABSTRACT

A surgical instrument and method are provided for guiding a cutting tool to resect an anatomical structure. The surgical instrument includes a guide body formed of a guide body material having a guide body material hardness, and a first bearing and a second bearing formed of a bearing material having a bearing material hardness. The bearing material hardness is greater than the guide body material hardness. The first bearing and the second bearing are secured to the guide body with at least a portion of the first bearing and at least a portion of the second bearing exposed from the guide body. Also, the second bearing is spaced a distance from the first bearing. By arranging the first bearing and the second bearing in this manner, the first bearing and the second bearing provide a discontinuous bearing surface for a cutting tool to contact when moving within the guide body. Additionally, the first bearing and the second bearing are each sized and arranged so that with the cutting tool positioned for guiding by the surgical instrument, the first bearing and the second bearing prevent contact between the cutting tool and the guide body.

20 Claims, 4 Drawing Sheets

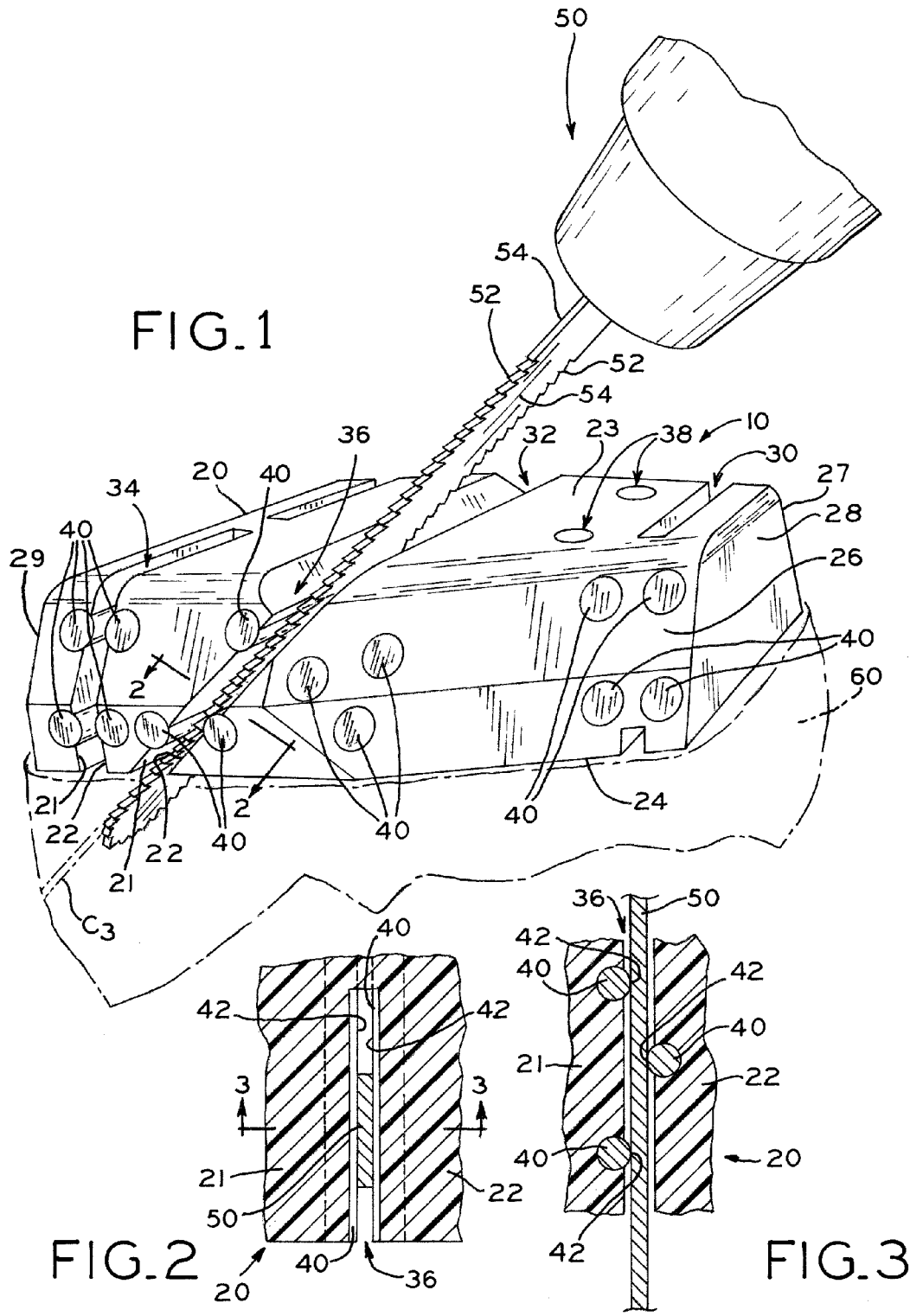

COMPOSITE SURGICAL INSTRUMENT

BACKGROUND

1. Field of the Invention

The present disclosure relates to surgical instruments. More particularly, the present disclosure relates to surgical cut guides.

2. Description of the Related Art

During an orthopedic procedure, an anatomical structure such as bone may be cut to allow implantation of a prosthesis. To ensure such cuts are properly positioned, and that adjacent tissue is not unnecessarily damaged, surgical instruments called cut guides are removably secured relative to the resection site and are used to guide a cutting tool to make appropriate cuts on the relevant tissue, e.g., bone.

Typical cut guides are made entirely of a surgical grade material, such as stainless steel, which is strong enough to be able to withstand the mechanical forces and the abrasive wear transferred to it by a cutting tool, such as a spinning drill bit, an oscillating saw, or a reciprocating saw. However, these cut guides are expensive to manufacture because the entire cut guide is made of a material of sufficient durability to act as a bearing for a moving cutting instrument. Further, these cut guides are reused because they are too expensive to be disposed of after a single use. For these cutting guides to be reusable, the cut guide must be properly cleaned and sterilized before reuse. Cleaning and sterilizing methods create additional costs and can be time consuming.

An example of a cut guide made of two separate materials is iJig® Pre-Navigated Instrumentation, available from Conformis, Inc. of Burlington, Mass. (iJig® is a registered trademark of Conformis, Inc. of Burlington, Mass.). This guide is a patient specific instrument and is customized to fit a particular patient's anatomy. The Conformis iJig® guide comprises a template made from an inexpensive material, such as plastic, and a guide made from a hard material, such as metal. The metal guide is attached to the template in an appropriate location and orientation to prevent a cutting tool from contacting the template when using the cutting tool to make appropriate cuts on a section of tissue. For example, a protective metal guide sheath lines a guide cavity of the template, which receives a drill bit therethrough, to provide a continuous bearing surface to guide the drill bit. Alternatively, a protective metal plate covers a planar guide surface of the template, which guides a cutting tool, to provide a continuous bearing surface to guide a cutting tool, such as a saw during a resection.

SUMMARY

The present disclosure provides a surgical instrument having a bearing arrangement designed to withstand the forces applied by surgical cutting tools and which is less costly to manufacture than the devices identified in the preceding paragraphs. The present disclosure provides a surgical instrument having a discontinuous bearing surface. A method of using such a surgical tool is also disclosed.

In one aspect of the present disclosure, the surgical instrument comprises a guide body formed of a guide body material having a guide body material hardness, and a first bearing and a second bearing formed of a bearing material having a bearing material hardness. The bearing material hardness is greater than the guide body material hardness. The first bearing and the second bearing are secured to the guide body with at least a portion of the first bearing and at least a portion of the second bearing exposed from the guide body. Also, the second bearing is spaced a distance from the first bearing. By arranging the first bearing and the second bearing in this manner, the first bearing and the second bearing provide a discontinuous bearing surface for a cutting tool to contact when moving within the guide body. Additionally, the first bearing and the second bearing prevent contact between the cutting tool and the guide body. In one embodiment, the guide body material comprises an inexpensive material such as plastic, and the bearing material comprises a surgical grade material such as stainless steel. A surgical instrument in accordance with the present disclosure, by having a discontinuous bearing surface, allows the amount of expensive surgical grade bearing material used to create the bearing surface to be significantly reduced as compared to the devices identified in the background section of this document, thereby reducing the cost of the surgical instrument. By reducing the manufacturing cost of the surgical instrument, disposable cut guide technologies are enabled. In another aspect of the present disclosure, the surgical instrument is particularly sized for use with a cutting tool, the surgical instrument guiding the cutting tool to resect an anatomical structure.

In yet another aspect of the present disclosure, a combination includes a cutting tool and a surgical instrument for guiding the cutting tool to resect an anatomical structure. The cutting tool includes a rotary cutting tool and the surgical instrument includes a guide body. The guide body defines a cavity that is sized to receive and guide the rotary cutting tool. In this embodiment, the surgical instrument includes three bearings formed of bearing material. The bearings are each secured to the guide body with at least a portion of each of the bearings exposed from the guide body and are each spaced less than 180° degrees from each adjacent bearing. The bearings are each sized and arranged so that with the rotary cutting tool positioned in the cavity for guidance, the guide body avoids contact with the cutting tool.

In another aspect of the present disclosure, a combination includes a cutting tool and a surgical instrument for guiding the cutting tool to resect an anatomical structure. The surgical instrument includes a guide body which has a first guide wall and a second guide wall opposed to the first guide wall. The first guide wall and the second guide wall define a cut slot that is sized to receive and guide the cutting tool. In this embodiment, the surgical instrument includes a first bearing and a second bearing each secured to the first guide wall with at least a portion of the first bearing and the second bearing exposed from the first guide wall. The second bearing is spaced a distance from the first bearing. Further, a third bearing is secured to the second guide wall with at least a portion of the third bearing exposed from the second guide wall, and the third bearing is spaced a distance from the first bearing and the second bearing. Also, the first bearing, the second bearing, and the third bearing are each sized and arranged so that with the cutting tool positioned in the cut slot for guidance, the guide body avoids contact with the cutting tool. In another embodiment, the surgical instrument further includes a fourth bearing secured to the second guide wall with at least a portion of the fourth bearing exposed from the second guide wall. The fourth bearing is spaced a distance from the first bearing, the second bearing, and the third bearing. The first bearing, the second bearing, the third bearing, and the fourth bearing are each sized and arranged so that with the cutting tool positioned in the cut slot for guidance, the guide body avoids contact with the cutting tool.

In yet another aspect of the present disclosure, a method for guiding a cutting tool to resect an anatomical structure includes providing a surgical instrument which comprises a guide body formed of a guide body material having a guide body material hardness, and a first bearing and a second bearing formed of a bearing material having a bearing material hardness, the bearing material hardness being greater than the guide body material hardness. The first bearing and the second bearing are secured to the guide body with at least a portion of the first bearing and at least a portion of the second bearing exposed from the guide body. Also, the second bearing is spaced a distance from the first bearing to form a discontinuous bearing surface. Next, the surgical instrument is positioned relative to the relevant anatomical structure. Then the cutting tool is guided with the first bearing and the second bearing to resect the anatomical structure. In another embodiment, the surgical instrument further includes a third bearing formed of bearing material. The third bearing is secured to the guide body with at least a portion of the third bearing exposed from the guide body and the third bearing is spaced a distance from the first bearing and the second bearing. The third bearing guides the cutting tool with the first bearing and the second bearing to resect the anatomical structure. In yet another embodiment, the portion of the first bearing exposed from the guide body, the portion of the second bearing exposed from the guide body, and the portion of the third bearing exposed from the guide body substantially define tangents to a circle, and the first bearing, the second bearing, and the third bearing are each spaced less than 180° degrees from each adjacent bearing. In another embodiment, the cutting tool is guided along a desired trajectory to resect the anatomical structure, and the portion of the first bearing and the portion of the second bearing that are exposed from the guide body are substantially parallel to a plane defined by the desired trajectory of the cutting tool. In yet another embodiment, the surgical instrument further includes a fourth bearing formed of bearing material.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 1 is a perspective view of a surgical instrument illustrating the surgical instrument secured relative to an anatomical structure and a cutting tool received in a cut slot of the surgical instrument;

FIG. 2 is a cross-sectional view taken along line 2-2 of FIG. 1;

FIG. 3 is a cross-sectional view taken along line 3-3 of FIG. 2;

Corresponding reference characters indicate corresponding parts throughout the several views. The exemplifications set out herein illustrate exemplary embodiments of the invention, and such exemplifications are not to be construed as limiting the scope of the invention in any matter.

DETAILED DESCRIPTION

Figure 4:
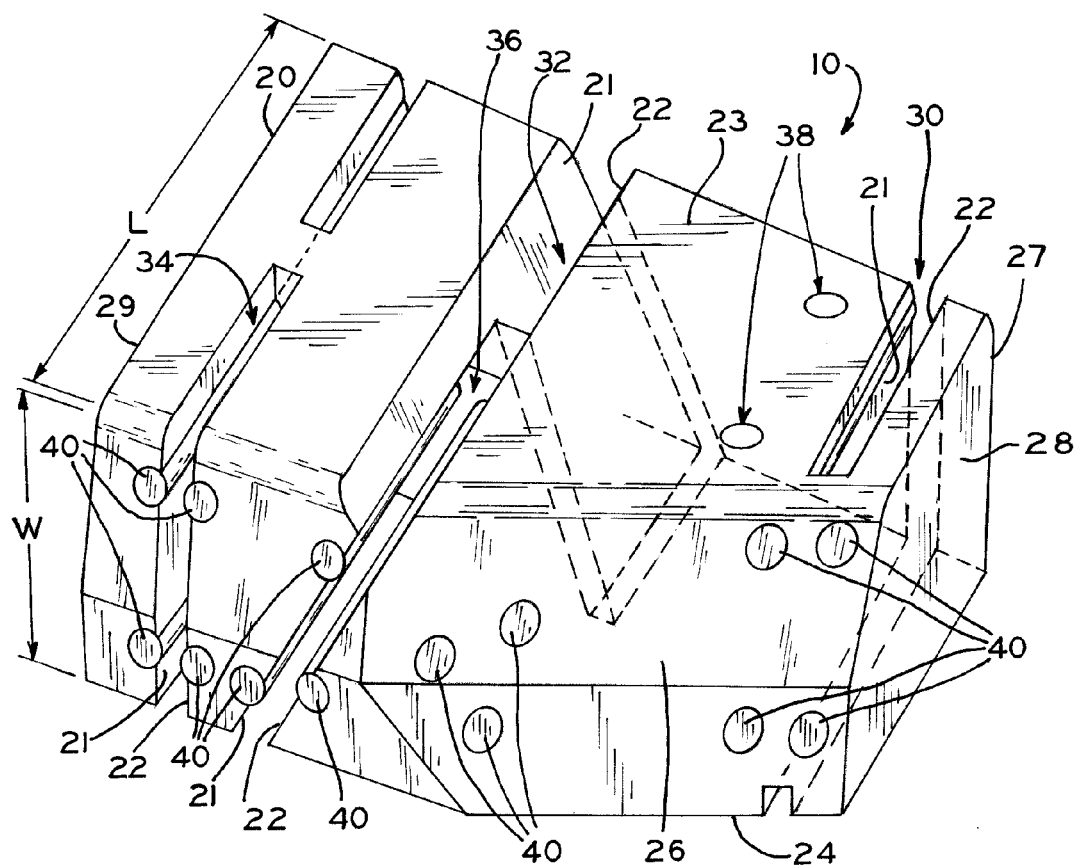
FIG. 4 is a perspective view of the surgical instrument of FIG. 1.
Figure 5:
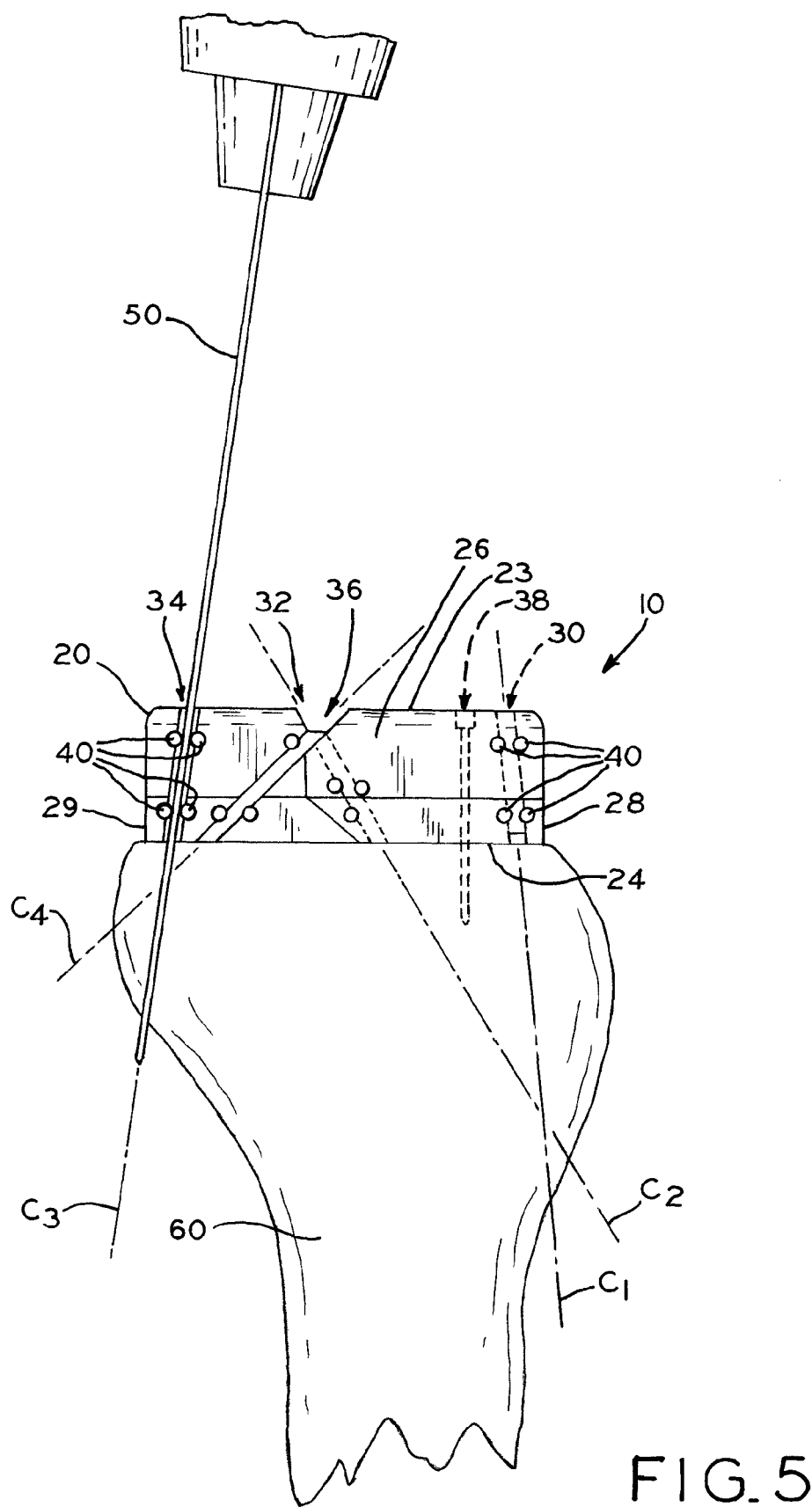
FIG. 5 is a side elevation view of the surgical instrument of FIG. 1 illustrating the surgical instrument secured relative to the anatomical structure and the cutting tool received in the cut slot of the surgical instrument.
Figure 6:
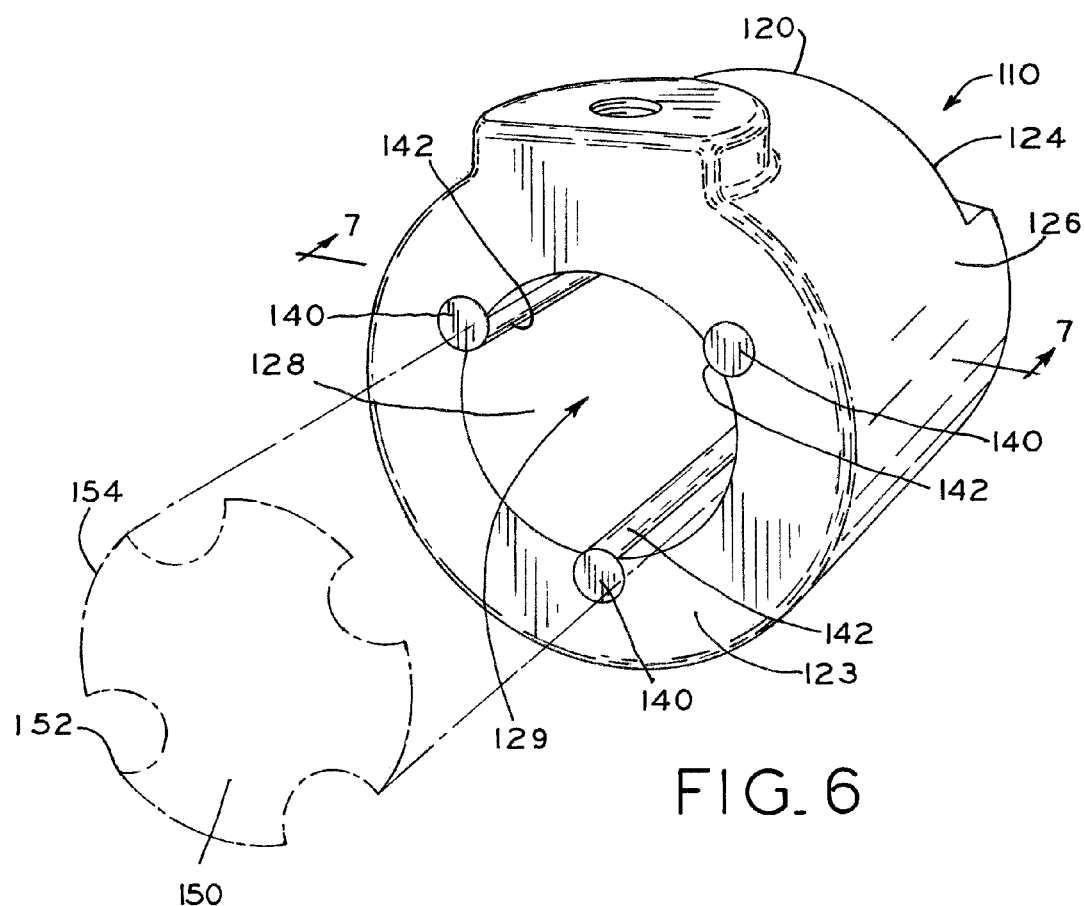
FIG. 6 is a perspective view of a surgical instrument in accordance with another exemplary embodiment of the present disclosure.
Figure 7:
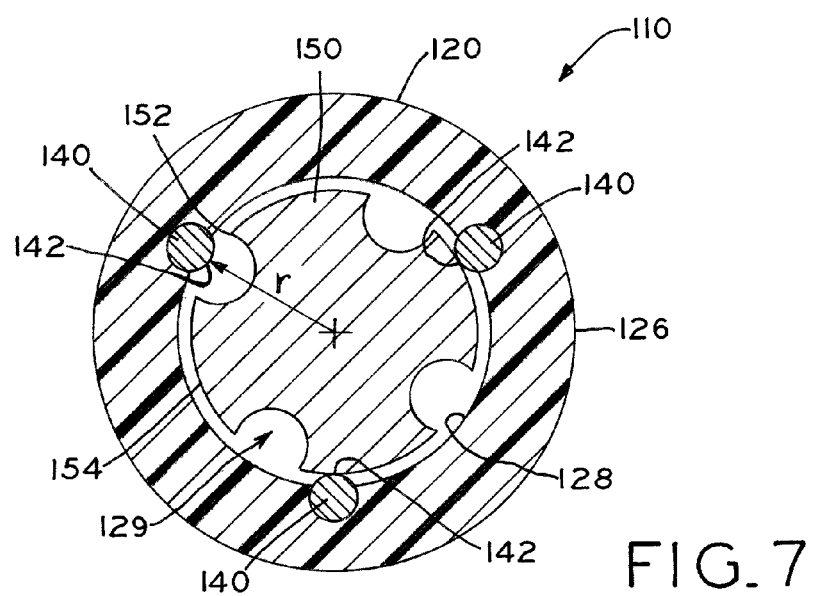
FIG. 7 is a cross-sectional view taken along line 7-7 of FIG. 6.

The present disclosure provides a surgical guide with a discontinuous bearing surface to guide a surgical instrument and prevent contact between the instrument and the guide. Such guides can be exemplified as a distal femoral cut guide as illustrated in FIGS. 1-5, or as a drill guide for guiding a rotary cutting instrument as illustrated in FIGS. 6 and 7.

FIG. 1 illustrates guide 10 according to an exemplary embodiment of the present disclosure. In the exemplary embodiment of FIG. 1, guide 10 is illustrated as a distal femoral cut guide positioned to guide the cutting of a femur so that the femur can receive a femoral component used in knee replacement surgery, though it is contemplated that other cut guides may be utilized in accordance with the present disclosure. Anatomical structure 60 is illustrated in FIGS. 1 and 5 as a distal end of a femur, though it is contemplated that a cut guide in accordance with the present disclosure can be secured relative to and used to resect other anatomical structures located throughout a body. Guide 10 may be made available in a variety of shapes and sizes to accommodate a variety of anatomical structures. For example, guide 10 may be manufactured to be a patient-specific guide which conforms to the surface of the anatomical structure. Patient-specific guides may be manufactured in accordance with the method and apparatuses described in U.S. Pat. No. 5,768,134, issued Jun. 16, 1998, entitled "Method for making a perfected medical model on the basis of digital image information of a part of the body", the disclosure of which is hereby expressly incorporated herein by reference.

Guide 10 generally includes guide body 20 having entry wall 23, exit wall 24 opposite entry wall 23, first perimeter wall 26, second perimeter wall 27 opposite first perimeter wall 26, third perimeter wall 28, and fourth perimeter wall 29 opposite third perimeter wall 28. Perimeter walls 26, 27, 28, 29 extend from entry wall 23 to exit wall 24. In the illustrated embodiment, a plurality of cut slots 30, 32, 34, 36, for receiving cutting tool 50 therethrough, extend through guide body 20 from entry wall 23 to exit wall 24. Each cut slot 30, 32, 34, 36 is defined by a first guide wall 21 and a second guide wall 22 opposite first guide wall 21, as best shown in FIG. 4. Referring to FIG. 1, cut slot 36 of guide body 20 is shown receiving cutting tool 50 therethrough. Each cut slot 30, 32, 34, 36 of guide body 20 is sized to cooperate with cutting tool 50. For example, each first guide wall 21 and each second guide wall 22, which define cut slot 30, 32, 34, 36, respectively, are spaced a distance apart to define a cut slot sized substantially to allow a reciprocating saw or oscillating saw to move along a planar cutting path defined by the opposing guide walls 21, 22. Cutting tool 50 includes opposing cutting tool cutting portions 52 defined by a plurality of teeth, and opposing cutting tool guide portions 54. In the illustrative embodiment of FIG. 1, cutting tool 50 is shown as a reciprocating saw in which the cutting action is achieved through a push and pull reciprocating motion of cutting tool cutting portions 52. Additionally, an oscillating saw in which the cutting action is achieved through a back and forth motion of a saw blade, or other similar saw, are suitable cutting tools that may be used with a surgical instrument of the present disclosure.

Guide body 20 is also provided with at least two bearings 40. Each bearing 40 is secured to guide body 20 so that at least a portion of each bearing 40 is exposed from guide body 20. Although guide body 20 does not itself directly guide cutting tool 50, guide body 20 sets the orientation of bearings 40, and bearings 40 guide cutting tool 50 to make resections in anatomical structure 60. Bearings 40 are each sized and arranged with guide body 20 so that with movement of cutting tool 50 within guide body 20, bearings 40 guide cutting tool 50 to make resections in anatomical structure 60 and prevent contact between cutting tool 50 and guide body 20. For example, referring to FIGS. 1 and 5, bearings 40 positioned within guide body 20 along anterior cut slot 30 guide cutting tool 50 to make anterior cut C1 shown in FIG. 5. Further, bearings 40 positioned within guide body 20 along anterior chamfer cut slot 32 guide cutting tool 50 to make anterior chamfer cut C2 shown in FIG. 5, and bearings 40 positioned within guide body 20 along posterior cut slot 34 guide cutting tool 50 to make posterior cut C3 shown in FIG. 5. Finally, bearings 40 positioned within guide body 20 along posterior chamfer cut slot 36 guide cutting tool 50 to make posterior chamfer cut C4 shown in FIG. 5. During a knee replacement orthopedic procedure, these cuts are made to the distal end of the femur to allow implantation of a prosthesis component.

Guide body 20 of the exemplary embodiment is made of a material that is less expensive than a bearing material of sufficient durability to act as a bearing for a moving cutting instrument to reduce the cost to produce guide 10. For example, guide body 20 may be formed of various plastics including polyethylene and polyphenylsulfone, and various metals such as aluminum that are less expensive than a bearing material of sufficient durability to act as a bearing for a moving cutting instrument. Further, it is contemplated that most polymers may be used for guide body 20, including thermoplastics, thermosets, and elastomers. Some examples of thermosetting plastics are Epoxy and phenolic, while nylon, polyethylene, and polystyrene are examples of thermoplastics. The important characteristics of the materials used to make guide body 20 is that they are less expensive than a bearing material of sufficient durability to act as a bearing for a moving cutting instrument and easy to machine. In an exemplary embodiment, guide body 20 is formed of a material having a guide body material hardness of sufficient rigidity to set the position and orientation of bearings 40. For example, guide body 20 can be formed of a material having a guide body material hardness of approximately 20 Shore A Hardness to approximately 95 Shore A Hardness. In alternate embodiments, guide body 20 can be formed of a material having a guide body material hardness of approximately 45 Shore D Hardness to approximately 85 Shore D Hardness, or approximately 50 Rockwell R Hardness (HRR) to approximately 150 Rockwell R Hardness (HRR).

Bearings 40 of the exemplary embodiment are preferably made of a surgical grade material, having a strength and hardness sufficient to provide a suitable bearing surface for cutting tool 50 to contact when moving within guide body 20. For example, bearings 40 may be formed of various metals such as stainless steel, various alloys such as a cobalt-chromium alloy, various ceramics such as silicon nitride and aluminum oxide, carbon fiber materials, and zirconia, though it is contemplated that other materials may be used. Each of the above-described bearing materials are of sufficient durability to act as a bearing for a moving cutting instrument. It is contemplated that bearings 40 have a bearing material hardness of approximately 70 Rockwell B Hardness (HRB) to approximately 95 Rockwell B Hardness (HRB), or approximately 25 Rockwell C Hardness (HRC) to approximately 41 Rockwell C Hardness (HRC). For example, bearings 40 having a bearing material hardness as described above, i.e., the approximate hardness values of stainless steel, will suffice for most applications. In an exemplary embodiment, the hardness of the bearing material is greater than the hardness of the guide body material. Bearings 40 provide a suitable bearing surface for cutting tool 50 to contact and ride against when moving within cut slot 30, 32, 34, 36 of guide body 20. Bearings 40 are also each sized and arranged to prevent cutting tool 50 from contacting guide body 20. Another advantage of integrating bearings 40 into guide body 20 is that bearings 40 reinforce the strength of guide body 20.

Referring to FIGS. 1 and 3, each bearing 40 is spaced a distance from the other bearings 40. By arranging bearings 40 in this manner, bearings 40 provide a discontinuous bearing surface for cutting tool 50 to contact when moving within guide body 20. Advantageously, by having a discontinuous bearing surface, the amount of surgical grade material needed to create the bearing surface is significantly reduced as compared to the devices identified in the background section of this document, thereby reducing the cost of guide 10. By reducing the manufacturing cost of guide 10, disposable cutting guide technologies are enabled. After using a guide in accordance with the present disclosure for a particular procedure, the guide could be thrown away. Disposable guide technologies would prevent medical practitioners from being burdened with the cleaning and sterilization procedures required to reuse surgical instruments, which can be expensive and time consuming.

Although the bearing surface provided by bearings 40 is discontinuous, bearings 40 still prevent cutting tool 50 from contacting guide body 20. As shown in FIGS. 2 and 3, bearings 40 are positioned so that cutting tool 50 is guided by bearings 40 and cutting tool 50 does not contact guide body 20. For example, referring to FIGS. 1-5, a first exemplary arrangement of bearings 40 is illustrated within guide body 20 along posterior chamfer cut slot 36. In this arrangement, three bearings 40 are positioned within guide body 20 along cut slot 36. Each bearing 40 is secured to guide body 20 so that at least a portion of each bearing 40 is exposed from guide body 20. Two bearings 40 are secured to first guide wall 21 of cut slot 36, and the two bearings 40 are spaced a distance from each other to provide a discontinuous guide surface. An additional bearing 40 is secured to second guide wall 22 of cut slot 36. The additional bearing 40 is spaced a distance from each of the two bearings 40 secured to first guide wall 21. In an exemplary embodiment, the additional bearing 40 secured to second guide wall 22 is positioned an approximately equal distance from entry wall 23 and exit wall 24. Because in this exemplary arrangement there is one bearing 40 secured to second guide wall 22, it is advantageous to centrally locate bearing 40 along second guide wall 22 to prevent cutting tool 50 from contacting guide body 20. Referring to FIG. 3, cutting tool 50 contacts the three bearings 40 at three separate areas, i.e., bearing contact areas 42. According to an exemplary embodiment, cutting tool 50 may not have to contact the three bearings 40 simultaneously because each cut slot 30, 32, 34, 36 can be sized to allow clearance space between bearings 40 and cutting tool 50 when cutting tool 50 is positioned within a particular cut slot.

As is apparent from FIG. 3, at least one bearing 40 is located on each opposing guide wall 21, 22 to prevent cutting tool 50 from contacting guide body 20. According to an exemplary embodiment, a first bearing 40 secured to first guide wall 21 of cut slot 36 is positioned close, e.g., approximately 1 mm, to an entry point where cutting tool 50 enters cut slot 36, and a second bearing 40 secured to first guide wall 21 of cut slot 36 is positioned close, e.g., approximately 1 mm, to an exit point where cutting tool 50 exits cut slot 36 to make cuts in anatomical structure 60. This arrangement ensures that cutting tool 50 does not contact guide body 20 at the entry point or the exit point if cutting tool 50 becomes canted relative to the trajectory of the cut slot.

A second exemplary arrangement of bearings 40 is illustrated within posterior cut slot 34, as shown in FIGS. 1 and 4. In this arrangement, four bearings 40 are positioned within guide body 20 along cut slot 34. Each bearing 40 is secured to guide body 20 so that at least a portion of each bearing 40 is exposed from guide body 20. This arrangement includes two bearings 40 being secured to first guide wall 21 of cut slot 34 and two bearings 40 being secured to second guide wall 22 of cut slot 34, the bearings 40 being spaced a distance from each other to provide a discontinuous guide surface. For example, a distance between bearings 40 can be approximately 1.27 cm (0.5 inch) or approximately 1 cm (0.3937 inch). In one embodiment, a first bearing 40 secured to first guide wall 21 of cut slot 34, and a first bearing 40 secured to second guide wall 22 of cut slot 34, are positioned close to an entry point where cutting tool 50 enters cut slot 34. Also, a second bearing 40 secured to first guide wall 21 of cut slot 34, and a second bearing 40 secured to second guide wall 22 of cut slot 34, are positioned close to an exit point where cutting tool 50 exits cut slot 34 to make cuts in anatomical structure 60. As previously discussed, this arrangement ensures that cutting tool 50 does not contact guide body 20 at the entry point or the exit point if cutting tool 50 becomes canted relative to the trajectory of the cut slot.

Although two exemplary arrangements of positioning bearings 40 within guide body 20 are discussed above, it is contemplated that other configurations of bearings 40, with a varying number of bearings 40, may be used in accordance with the present disclosure to guide cutting tool 50 to make cuts in anatomical structure 60 and prevent cutting tool 50 from contacting guide body 20.

According to an exemplary embodiment, as illustrated in FIG. 4, bearings 40 can extend within guide body 20 along length L of cut slots 30, 32, 34, 36. Further, bearings 40 can be positioned within guide body 20 parallel to the other bearings 40. In another exemplary embodiment, bearings 40 can extend within guide body 20 along width W of cut slots 30, 32, 34, 36. In this embodiment, bearings 40 are spaced a distance apart less than a width of cutting tool 50 to prevent cutting tool 50 from contacting guide body 20.

FIGS. 1-7 illustrate bearings 40 as elongated cylindrical members, though it is contemplated that other shapes and sizes of bearings 40 may be used. For example, bearings 40 can have other multi-sided polygon cross-sectional shapes, such as square or rectangular cross-sectional shapes. Also, bearings 40 may not be elongated. In such an embodiment, bearings 40 are spaced a distance apart less than a width of cutting tool 50 to prevent cutting tool 50 from contacting guide body 20. In an exemplary embodiment, bearings 40 may be spherically shaped bodies which are strategically integrated into guide body 20 at various locations. In alternative embodiments, bearings 40 may be various polyhedron or cube shaped bodies.

Guide body 20 also includes fixation holes 38 extending through guide body 20 from entry wall 23 to exit wall 24. Fixation holes 38 guide the placement of fixation pins or screws to secure guide body 20 to a desired anatomical structure 60.

Referring to FIG. 4, first guide wall 21 of cut slot 30 provides a planar guide surface, and bearings 40 located along first guide wall 21 of cut slot 30 provide a planar bearing surface, which may be utilized to guide cutting tool 50. As illustrated in FIG. 4, an opposing wall, i.e., second guide wall 22 of cut slot 30, can be added to provide a second planar guide surface, having bearings 40 located along second guide wall 22 to provide a second bearing surface. By having a second planar guide surface, cutting tool 50 can be prevented from lifting away from a first planar guide surface when cutting tool 50 is positioned within guide body 20. Additionally, first perimeter wall 26 can provide cut slot 30 with a terminal wall enclosing cut slot 30 on an additional side, as shown in FIG. 4. First perimeter wall 26 restricts the lateral movement of cutting tool 50 to reduce the chance of cutting tool 50 contacting an undesired portion of anatomical structure 60. Although FIG. 4 does not illustrate a wall enclosing cut slot 30 along second perimeter wall 27, cut slot 30 could have an additional terminal wall located along second perimeter wall 27 to further restrict the lateral movement of cutting tool 50.

Referring to FIG. 5, cutting tool 50 is guided along a desired trajectory C1, C2, C3, C4 to resect anatomical structure 60 at a variety of different locations. For example, as previously discussed, cutting tool 50 is guided along anterior cut trajectory C1 to make an anterior cut in a distal end of femur 60, cutting tool 50 is guided along anterior chamfer cut trajectory C2 to make an anterior chamfer cut in femur 60, cutting tool 50 is guided along posterior cut trajectory C3 to make a posterior cut in femur 60, and cutting tool 50 is guided along posterior chamfer cut trajectory C4 to make a posterior chamfer cut in femur 60. The angle and position of desired cut trajectories C1, C2, C3, and C4 may depend upon a variety of factors including the size of femur 60, the size of a selected femoral component, and the condition of femur 60. According to an exemplary embodiment, the portion of the bearings 40 that are exposed from guide body 20 are substantially parallel to a plane defined by the desired trajectory C1, C2, C3, C4 of cutting tool 50.

FIG. 6 illustrates guide 110 according to another exemplary embodiment of the present disclosure. In this exemplary embodiment, guide 110 comprises a drill guide for guiding rotary cutting tool 150, such as a drill bit, to form holes in anatomical structure 60. For example, rotary cutting tool 150 can drill holes in a femur so the femur can receive a fixation post of a femoral implant during knee replacement surgery. Rotary cutting tool 150 includes cutting tool cutting portion 152 and cutting tool guide portion 154.

Guide 110 includes guide body 120, guide body 120 defining exterior wall 126 and interior wall 128. Interior wall 128 defines cavity 129 which is sized to receive cutting tool 150 therethrough. Although guide body 120 is illustrated in FIGS. 6 and 7 as having an annular shape, it is contemplated that guide body 120 can comprise any regular or irregular shape that can hold bearings 140 so that bearing contact areas 142 substantially define tangents to a circle with radius r, as shown in FIG. 7. Guide body 120 also includes entry wall 123 and exit wall 124 opposite entry wall 123. Exterior wall 126 and interior wall 128 extend from entry wall 123 to exit wall 124. Guide 110 may be made available in a variety of shapes and sizes to accommodate a variety of different anatomical structures located throughout a body.

Referring to FIGS. 6 and 7, guide body 120 is provided with at least three bearings 140 secured to guide body 120. Each bearing 140 is secured to guide body 120 so that at least a portion of each bearing 140 is exposed from guide body 120. Although guide body 120 does not itself directly guide cutting tool 150, guide body 120 sets the orientation of bearings 140, and bearings 140 guide cutting tool 150 to drill holes in a desired anatomical structure. Bearings 140 are each sized and arranged with guide body 120 so that with movement of cutting tool 150 within guide body 120, bearings 140 guide cutting tool 150 to drill holes in an anatomical structure and prevent contact between cutting tool 150 and guide body 120.

As previously discussed with respect to guide body 20, guide body 120 is made of a material that is less expensive than a bearing material of sufficient durability to act as a bearing for a moving cutting instrument, such as plastic, to reduce the cost to produce guide 110. The materials used to make guide body 120 are the same as the materials used to make guide body 20. Further, as previously discussed with respect to bearings 40, bearings 140 are made of a surgical grade material, such as stainless steel, to provide a suitable bearing surface for cutting tool 150 to contact when moving within guide body 120. The materials used to make bearings 140 are the same as the materials used to make bearings 40.

Referring to FIGS. 6 and 7, each bearing 140 is spaced a distance from the other bearings 140. By arranging bearings 140 in this manner, bearings 140 provide a discontinuous bearing surface for cutting tool 150 to contact when moving within guide body 120 and prevent contact between cutting tool 150 and guide body 120. Advantageously, as previously discussed with respect to guide 10, by having a discontinuous bearing surface, the amount of surgical grade material needed to create the bearing surface is significantly reduced as compared to the devices identified in the background section of this document, thereby reducing the cost of guide 110.

Although the bearing surface provided by bearings 140 is discontinuous, bearings 140 still prevent cutting tool 150 from contacting guide body 120. As shown in FIG. 7, bearings 140 are positioned so that cutting tool 150 is guided by bearings 140 and cutting tool 150 does not contact guide body 120. For example, referring to FIGS. 6 and 7, an exemplary arrangement of bearings 140 is illustrated within guide body 120. In this arrangement, three bearings 140 are positioned within guide body 120. In one embodiment, the three bearings 140 are spaced an equal distance apart around the circumference of interior wall 128 of guide body 120 to provide a discontinuous bearing surface for cutting tool 150 to contact when moving within cavity 129. In this embodiment, each bearing 140 is spaced apart approximately 120° degrees from the other two bearings 140. In other embodiments, bearings 140 may not be spaced apart 120° degrees from each other. In an exemplary embodiment, each of the bearings 140 are spaced less than 180° degrees from each adjacent bearing 140 to ensure that bearings 140 guide cutting tool 150 so that cutting tool 150 does not contact guide body 120.

Referring to FIG. 7, cutting tool 150 contacts the three bearings 140 at three separate areas, i.e., bearing contact areas 142. According to an exemplary embodiment, cutting tool 150 may not have to contact the three bearings 140 simultaneously because guide body 120 can be sized to allow clearance space between bearings 140 and cutting tool 150 when cutting tool 150 is positioned within guide body 120.

As previously discussed with respect to guide body 20, in one embodiment, bearings 140 extend the length of guide body 120, and each bearing 140 can be positioned within guide body 120 parallel to the other bearings 140. In another exemplary embodiment, bearings 140 can extend along a circumference of interior wall 128. Further, bearings 140 are illustrated as elongated cylindrical members, though it is contemplated that other shapes and sizes of bearings 140 may be used. For example, bearings 140 can have other multi-sided polygon cross-sectional shapes, such as square or rectangular cross-sectional shapes. Also, bearings 140 may be spherically shaped bodies which are strategically integrated into guide body 120 at various locations. As mentioned above, bearings 140 may also be other non-elongated shapes such as various polyhedron or cube shaped bodies.

As previously discussed, during an orthopedic procedure, an anatomical structure such as bone may be resected to allow implantation of a prosthesis. To ensure such cuts are properly positioned, and that adjacent tissue is not unnecessarily damaged, a cut guide is positioned relative to an appropriate anatomical structure, and is used to guide a cutting tool to make appropriate cuts on relevant tissue, e.g., bone. Referring to FIG. 5, in an illustrative procedure in accordance with the present disclosure, a surgeon selects a surgical instrument, such as guide 10, having guide body 20 formed of a guide body material having a guide body material hardness, and at least two bearings 40 formed of a bearing material having a bearing material hardness, the bearing material hardness greater than the guide body material hardness. Bearings 40 are secured to guide body 20 with at least a portion of bearings 40 exposed from guide body 20. Each bearing 40 is spaced a distance from other bearings 40. Once the surgeon selects the surgical instrument, the surgeon then positions guide 10 relative to anatomical structure 60 so an appropriate resection to anatomical structure 60 can be made. When the surgeon is satisfied with the positioning of guide 10 relative to anatomical structure 60, a desired cutting tool is selected, such as cutting tool 50. As previously discussed, a reciprocating saw, an oscillating saw, a drill bit, or similar cutting tool can be selected. Next, the surgeon guides the selected cutting tool 50 with bearings 40 to make resections in a desired portion of anatomical structure 60. FIG. 5 illustrates cutting tool 50 guided along posterior cut trajectory C3 to make a posterior cut in femur 60. Bearings 40 are positioned within guide body 20 along posterior cut slot 34 to ensure that cutting tool 50 cuts anatomical structure 60 along posterior cut trajectory C3 and prevents cutting tool 50 from contacting guide body 20. Additional bone resections are made as necessary to finish femur 60 in accordance with the steps discussed above to allow implantation of a prosthesis.

Guide 10, 110 may be made by a variety of methods. For example, guide body 20, 120 and bearings 40, 140 may be made using insert injection molding. Bearings 40, 140 may be placed into a mold cavity and positioned according to a desired bearing arrangement. Next, a desired polymer material, such as plastic, to be used to make guide body 20, 120 is converted into a liquid state and then injected into the mold cavity containing bearings 40, 140. Once the molten polymer material saturates the mold, the mold is cooled leaving the guide body and the bearings fused together. It is contemplated that other methods may also be used to form guide body 20, 120. For example, guide body 20, 120 may be cast, machined, compression molded, injection molded, blow molded, stamped, punched, and/or otherwise formed using similar manufacturing methods. After guide body 20, 120 is manufactured, bearings 40, 140 can then be secured to guide body 20, 120 using a variety of techniques, such as cutting appropriate sized grooves in guide body 20, 120 and then securing bearings 40, 140 within the grooves.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument for guiding a cutting tool, the surgical instrument comprising:
a guide body including a cut slot defined by a first guide wall and a second guide wall opposing said first guide wall, each of said first guide wall and said second guide wall being formed of a guide body material having a guide body material hardness;

a first bearing formed of a bearing material having a bearing material hardness, the bearing material hardness greater than the guide body material hardness, said first bearing secured to said guide body with at least a portion of said first bearing extending from said first guide wall into said cut slot and defining a first bearing surface; and a second bearing formed of the bearing material, said second bearing secured to said guide body with at least a portion of said second bearing extending from said second guide wall into said cut slot and defining a second bearing surface, opposing said first bearing surface.

2. The surgical instrument of claim 1, wherein the surgical instrument further comprises a third bearing formed of the bearing material, said third bearing secured to said guide body with at least a portion of said third bearing extending from said first guide wall into said cut slot and defining a third bearing surface, said third bearing spaced a distance from said first bearing such that said first bearing surface and said third bearing surface are not contiguous.

3. The surgical instrument of claim 2, wherein said first bearing surface, said second bearing surface, and said third bearing surface substantially define tangents to a circle, and said first bearing surface, said second bearing surface, and said third bearing surface are each spaced less than 180 degrees from each adjacent bearing surface.

4. The surgical instrument of claim 2, wherein said first bearing is disposed proximal to the entrance of the cut slot, said third bearing is disposed proximal to the exit of the cut slot, and said second bearing is disposed on said second guide wall in a region between said first bearing and said third bearing.

5. The surgical instrument of claim 2, further comprising a fourth bearing formed of the bearing material, said fourth bearing secured to said guide body with at least a portion of said fourth bearing extending from said second guide wall into said cut slot and defining a fourth bearing surface, said fourth bearing spaced a distance from said second bearing such that said second bearing surface and said fourth bearing surface are not contiguous.

6. The surgical instrument of claim 1, wherein said first bearing surface is arranged to contact a first surface of said cutting tool and said second bearing surface is arranged to contact a second surface of said cutting tool, opposite the first surface of said cutting tool.

7. The surgical instrument of claim 1, wherein the bearing material hardness is approximately 25 HRC to approximately 41 HRC.

8. The surgical instrument of claim 1, wherein said guide body material hardness is approximately 50 HRR to approximately 150 HRR.

9. A system, comprising:
a rotary cutting tool including a guide surface and a cutting surface; and
a surgical instrument for guiding said rotary cutting tool to resect an anatomical structure, said surgical instrument comprising:
  a guide body formed of a guide body material having a guide body material hardness, said guide body defining a cavity sized to receive and guide said rotary cutting tool;
  a first bearing, a second bearing and a third bearing, each one of said first, second and third bearings formed of a bearing material having a bearing material hardness greater than the guide body material hardness, each one of said first, second and third bearings secured to said guide body adjacent to said cavity with at least a portion of each one of said first, second and third bearings extending from said guide body into said cavity,
  wherein said first bearing, said second bearing and said third bearing substantially define tangents to a circle, said first bearing, said second bearing and said third bearing are spaced less than 180 degrees from each adjacent bearing, and wherein each one of said first, second and third bearings is sized and arranged so that with said rotary cutting tool positioned in said cavity, said guide body avoids contact with said rotary cutting tool.

10. The system of claim 9, wherein:
said guide body includes a first guide wall and a second guide wall opposed to said first guide wall, said first guide wall and said second guide wall defining a cut slot, said cut slot sized to receive and guide said rotary cutting tool;
said first bearing secured to said first guide wall;
said second bearing secured to said first guide wall; and
said third bearing secured to said second guide wall.

11. The system of claim 10, further comprising a fourth bearing formed of the bearing material, said fourth bearing secured to said second guide wall with at least a portion of said fourth bearing extending from said second guide wall into said cavity, said fourth bearing spaced a distance from said first bearing, said second bearing, and said third bearing;
wherein said first bearing, said second bearing, said third bearing, and said fourth bearing are each sized and arranged so that with said rotary cutting tool positioned in said cut slot, said guide body avoids contact with said rotary cutting tool.

12. The system of claim 9, wherein said guide body material hardness is approximately 50 HRR to approximately 150 HRR.

13. The system of claim 9, wherein the bearing material hardness is approximately 25 HRC to approximately 41 HRC.

14. A method for guiding a cutting tool to resect an anatomical structure, the method comprising:
providing or receiving a cutting tool;
providing or receiving a surgical instrument comprising:
  a guide body including a cut slot defined by a first guide wall and a second guide wall opposing said first guide wall, wherein each of said first guide wall and said second guide are formed of a guide body material having a guide body material hardness;
  a first bearing formed of a bearing material having a bearing material hardness, the bearing material hardness greater than the guide body material hardness, the first bearing secured to the guide body with at least a portion of the first bearing extending from the guide body into the cut slot and defining a first bearing surface;
  a second bearing formed of the bearing material, the second bearing secured to the second guide wall with at least a portion of the second bearing extending from the second guide wall into the cut slot and defining a second bearing surface, the first bearing surface opposing the second bearing;
positioning the surgical instrument relative to the anatomical structure; and
guiding the cutting tool, including guiding a first surface of the cutting tool with the first bearing surface and concurrently guiding a second surface of the cutting tool, opposite the first surface, with the second bearing surface to resect the anatomical structure such that said first surface of the cutting tool avoids contact with said first guide wall and the second surface of the cutting tool avoids contact with said second guide wall.

15. The method of claim 14, wherein the surgical instrument further comprises a third bearing formed of the bearing material, the third bearing secured to the guide body with at least a portion of the third bearing extending from the first guide wall into said cut slot and defining a third bearing surface, the third bearing spaced a distance from the first bearing, wherein the step of guiding the cutting tool includes the third bearing surface guiding the first surface of the cutting tool with the first bearing surface such that said the first surface of the cutting tool avoids contact with said first guide wall.

16. The method of claim 15, wherein the surgical instrument further comprises a fourth bearing formed of the bearing material, the fourth bearing secured to the guide body with at least a portion of the fourth bearing extending from the second guide wall into the cut slot and defining a fourth bearing surface, the fourth bearing spaced a distance from the second bearing, and wherein guiding the cutting tool includes the fourth bearing surface guiding the second surface of the cutting tool with the second bearing surface such that said the second surface of the cutting tool avoids contact with said second guide wall.

17. The method of claim 14, wherein the first bearing surface, the second bearing surface, and the third bearing surface substantially define tangents to a circle, and the first bearing, the second bearing and the third bearing are spaced less than 180 degrees from each adjacent bearing.

18. The method of claim 14, wherein the cutting tool is guided along a desired trajectory to resect the anatomical structure, and the first bearing surface and the second bearing surface are substantially parallel to a plane defined by the desired trajectory of the cutting tool.

19. The method of claim 14, wherein the guide body material hardness is approximately 50 HRR to approximately 150 HRR.

20. The method of claim 14, wherein the bearing material hardness is approximately 25 HRC to approximately 41 HRC.

* * * * *